(12) United States Patent
Brodsky et al.

(10) Patent No.: US 9,784,743 B2
(45) Date of Patent: Oct. 10, 2017

(54) COLLAGENS AS MARKERS FOR BREAST CANCER TREATMENT

(71) Applicant: Rhode Island Hospital, A Lifespan-Partner, Providence, RI (US)

(72) Inventors: Alexander S. Brodsky, Newton, MA (US); Yihong Wang, Sharon, MA (US); Murray Resnick, Sharon, MA (US)

(73) Assignee: Rhode Island Hospital, A Lifespan-Partner, Providence, RI (US)

( * ) Notice: Subject to any disclaimer, the term of this patent is extended or adjusted under 35 U.S.C. 154(b) by 0 days.

(21) Appl. No.: 15/187,279

(22) Filed: Jun. 20, 2016

(65) Prior Publication Data

US 2016/0370371 A1 Dec. 22, 2016

Related U.S. Application Data

(60) Provisional application No. 62/183,086, filed on Jun. 22, 2015.

(51) Int. Cl.
*G01N 33/574* (2006.01)
*C12Q 1/68* (2006.01)

(52) U.S. Cl.
CPC ..... *G01N 33/57415* (2013.01); *C12Q 1/6886* (2013.01); *C12Q 2600/106* (2013.01); *C12Q 2600/158* (2013.01); *G01N 2333/485* (2013.01); *G01N 2333/723* (2013.01); *G01N 2333/78* (2013.01); *G01N 2800/52* (2013.01)

(58) Field of Classification Search
None
See application file for complete search history.

(56) References Cited

U.S. PATENT DOCUMENTS

| 2010/0130377 A1 | 5/2010 | Vasmatzis et al. |
| 2014/0235486 A1 | 8/2014 | Chapman et al. |

OTHER PUBLICATIONS

Ferguson et al. (Cancer Res., 65: 8209-8217, 2005).*
Desmedt et al., "Characterization and Clinical Evaluation of CD10+ Stroma Cells in the Breast Cancer Movement," Clin. Cancer Res., 18(4):1004-1014 (2012).
Ferguson et al., "Selective Identification of Secreted and Transmembrane Breast Cancer Markers Using *Escherichia coli* Ampicillin Secretion Trap," Cancer Res., 65(18):8209-8217 (2005).

* cited by examiner

*Primary Examiner* — Brad Duffy
*Assistant Examiner* — Nelson B Moseley, II
(74) *Attorney, Agent, or Firm* — Fish & Richardson P.C.

(57) ABSTRACT

The specification provides methods of determining whether a subject suffering from ER+/HER2+ breast cancer is likely to respond to adjuvant and neoadjuvant chemotherapy and methods of treating a subject suffering from ER+/HER2+ breast cancer.

16 Claims, 6 Drawing Sheets

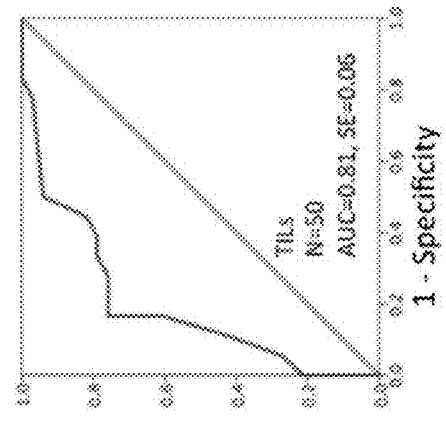
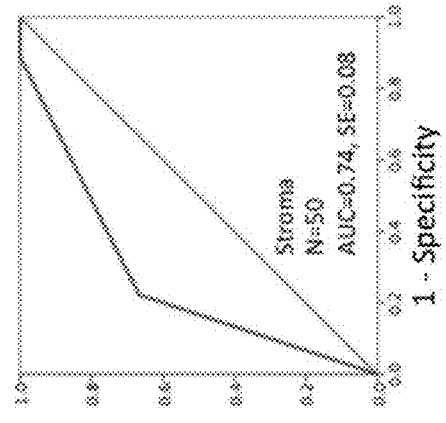
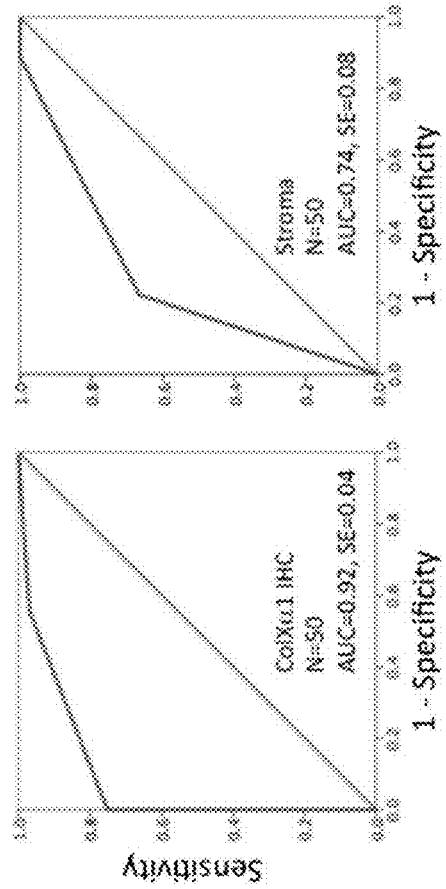
FIG. 3A
FIG. 3B
FIG. 3C
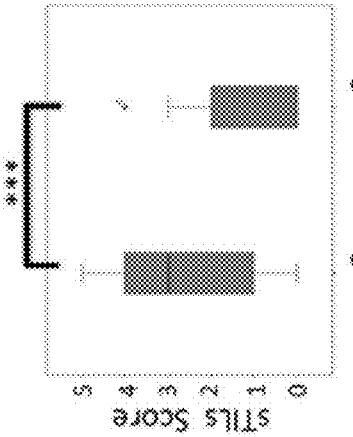
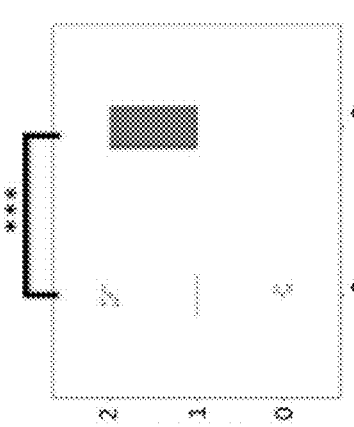
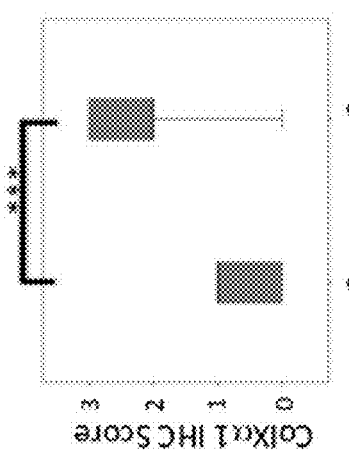
FIG. 3D
FIG. 3E
FIG. 3F

COLLAGENS AS MARKERS FOR BREAST CANCER TREATMENT

CROSS REFERENCE TO RELATED APPLICATIONS

This application claims the benefit of U.S. Application No. 62/183,086, filed on Jun. 22, 2015, the entire contents of which are hereby incorporated by reference in its entirety.

TECHNICAL FIELD

The claimed methods relate to biomarkers of breast cancer and methods of use thereof.

BACKGROUND

Breast carcinomas represent a heterogeneous group of tumors at the clinical, histopathologic, and molecular levels (Cancer Genome Atlas Network, *Nature* 490:61-70, 2012). The diversity of breast carcinoma is increasingly reflected in the diversification of therapeutic approaches that are based on appropriate biomarkers. For example, classification by estrogen receptor (ER), human epidermal growth factor receptor 2 (HER2), and progesterone receptor (PR) is routinely used in clinical practice as a guide for the selection of therapy for breast cancer subjects.

Neoadjuvant chemotherapy (NAC) allows for rapid assessment of treatment chemosensitivity (DeMichele et al., *Clin Cancer Res* 2015. doi: 10.1158/1078-0432.CCR-14-1760. PubMed PMID: 25712686). The post-treatment pathologic response can be used to determine efficacy of new systemic therapies, and to tailor further treatment that is most appropriate for the particular subject. Pathological complete response (pCR) is an acceptable surrogate associated with long term outcomes, but despite the addition of anti-HER2 therapy (trastuzumab) and even dual anti-HER2 therapy (trastuzumab with pertuzumab or lapatinib), pCR rates remain low in ER+/HER2+ cases compared with ER−/HER2+ disease, as data presented in a NeoSPHERE, NeoALTTO, and TRYPHAENA trial (Schneeweiss et al., *Annals of Oncology* 24:2278-2284, 2013; Carey, *J Clin Oncol* 30:1909-1911, 2012; Gianni et al., *Lancet Oncology*, 13:25-32, 2012). Also, pCR rates are substantially lower in ER+ vs. ER− diseases that are HER2−, motivating investigation into other parameters that are mediating response.

SUMMARY

The present invention is based, at least in part, on the discovery that low expression levels of Col10A1 mRNA and ColXα1 protein, high levels of total tumor infiltrating lymphocytes (tTILs), low levels of tumor-associated stroma, and low expression levels of Col3A1 mRNA, ColIIIα1 protein, Col14A1 mRNA, and ColXIVα1 protein are associated with pathologic complete response (pCR) to adjuvant and neoadjuvant chemotherapy with (NAC+H) or without (NAC−H) HER2-targeted therapy in ER+/HER2+ breast cancer subtypes. Thus, measurement of Col10A1 mRNA and/or ColXα1 protein expression with or without a determination of the amount of tTILs, tumor-associated stroma, Col3A1 mRNA, ColIIIα1 protein, Col14A1 mRNA, and/or ColXIVα1 protein can be used to identify subjects most likely to respond to adjuvant and neoadjuvant chemotherapy with (NAC+H) or without (NAC−H) HER2-targeted therapy and provide methods of treating a subject diagnosed as having ER+/HER2+ breast cancer.

In one aspect, the present disclosure provides methods of treating a subject, e.g., a human, diagnosed as having estrogen receptor positive and human epidermal growth factor receptor 2 positive breast cancer, the method including providing a sample comprising cancerous breast tissue from the subject; detecting in the sample an expression level of collagen type 10 alpha 1 that is the same or lower than a collagen type 10 alpha 1 reference level; administering an adjuvant and/or neoadjuvant chemotherapy to the subject.

In some embodiments, the methods include detecting in the sample an expression level of collagen type 3 alpha 1 that is the same or lower than a collagen type 3 alpha 1 reference level.

In some embodiments, the methods include detecting in the sample an expression level of collagen type 14 alpha 1 that is the same or lower than a collagen type 14 alpha 1 reference level.

In some embodiments, the methods include detecting in the sample a total level of tumor infiltrating T lymphocytes (tTILs) that is the same or greater than a tTILs reference level.

In some embodiments, the methods include detecting in the sample a level of tumor-associated stroma that is the same or lower than a tumor-associated stroma reference level.

In some embodiments, the expression level of collagen type 10 alpha 1 mRNA is detected by Northern blot or qPCR analysis. In some embodiments, the expression level of collagen type 10 alpha 1 protein is detected by immunohistochemistry.

In some embodiments, the expression level of collagen type 3 alpha 1 mRNA is detected by Northern blot or qPCR analysis. In some embodiments, the expression level of collagen type 3 alpha 1 protein is detected by immunohistochemistry.

In some embodiments, the expression level of collagen type 14 alpha 1 mRNA is detected by Northern blot or qPCR analysis. In some embodiments, the expression level of collagen type 14 alpha 1 protein is detected by immunohistochemistry.

In some embodiments, the neoadjuvant chemotherapy comprises administering docetaxel, carboplatin, doxorubicin, cyclophosphamide, paclitaxel, or a combination thereof. In some embodiments, the adjuvant chemotherapy comprises administering docetaxel, carboplatin, doxorubicin, cyclophosphamide, paclitaxel, or a combination thereof.

In some embodiments, the methods include administering a HER2-targeted therapy, e.g., trastuzumab, pertuzumab, lapatinib, or a combination thereof.

In another aspect, methods of treating a subject, e.g., a human, diagnosed as having estrogen receptor positive and human epidermal growth factor receptor 2 positive breast cancer are featured that include providing a sample comprising cancerous breast tissue from the subject; detecting in the sample an expression level of collagen type 10 alpha 1 protein (ColXα1) that is the same or greater than a ColXα1 reference level; and administering a drug targeted to ColXα1 to the subject, e.g., an anti-ColXα1 antibody conjugated to the drug.

In some embodiments, the anti-ColXα1 antibody is a monoclonal antibody or antigen-binding fragment thereof that selectively binds to ColXα1.

In some embodiments, the expression level of ColXα1 is determined by immunohistochemistry.

In some embodiments, the methods include detecting in the sample an expression level of collagen type 3 alpha 1 protein (ColIIIα1) that is the same or greater than a ColIIIα1 reference level; and administering a drug targeted to ColIIIα1 to the subject, e.g., an anti-ColIIIα1 antibody conjugated to the drug.

In some embodiments, the anti-ColIIIα1 antibody is a monoclonal antibody or antigen-binding fragment thereof that selectively binds to ColIIIα1.

In some embodiments, the expression level of ColIIIα1 is determined by immunohistochemistry.

In some embodiments, the methods include detecting in the sample an expression level of collagen type 14 alpha 1 protein (ColXIVα1) that is the same or greater than a ColXIVα1 reference level; and administering a drug targeted to ColXIVα1 to the subject, e.g., an anti-ColXIVα1 antibody conjugated to the drug.

In some embodiments, the anti-ColXIVα1 antibody is a monoclonal antibody or antigen-binding fragment thereof that selectively binds to ColXIVα1.

In some embodiments, the expression level of ColXIVα1 is determined by immunohistochemistry.

In some embodiments, the methods include administering a neoadjuvant chemotherapy, e.g., docetaxel, carboplatin, doxorubicin, cyclophosphamide, and/or paclitaxel, and/or an adjuvant chemotherapy, e.g., docetaxel, carboplatin, doxorubicin, cyclophosphamide, and/or paclitaxel.

In some embodiments, the methods include administering a HER2-targeted therapy, e.g., trastuzumab, pertuzumab, or lapatinib.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3A shows a ROC analysis of ColXα1 IHC scores. AUC=Area Under the Curve, SE=Standard Error.

FIG. 3B shows a ROC analysis of stroma scores. AUC=Area Under the Curve, SE=Standard Error.

FIG. 3C shows a ROC analysis of percent TILs. AUC=Area Under the Curve, SE=Standard Error.

FIG. 3D shows the distinct separation between tumors with pCR and those that with no pCR based on ColXα1 IHC scores. * $P<0.05$ ***, $P<0.001$.

FIG. 3E shows the distinct separation between tumors with pCR and those that with no pCR based on stroma scores. * $P<0.05$ ***, $P<0.001$.

FIG. 3F shows the distinct separation between tumors with pCR and those that with no pCR based on percent TILs. * $P<0.05$ ***, $P<0.001$.

DETAILED DESCRIPTION

Figure 1A:
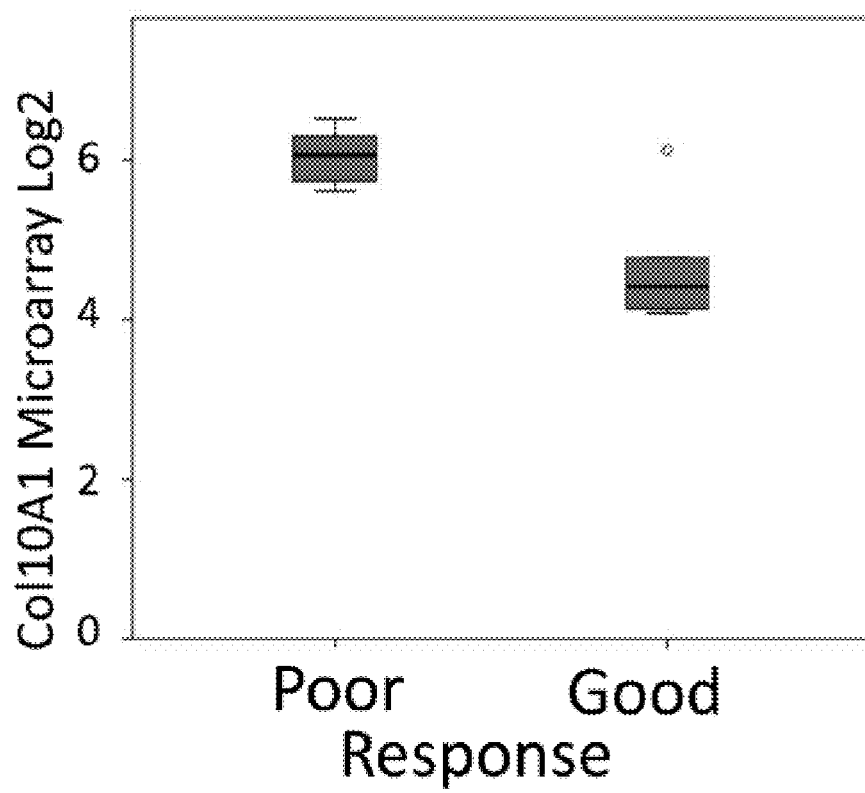
FIG. 1A is a box plot showing an association between Col10A1 expression with NAC response from a probeset on the Affymetrix HTA 2.0 microarray, distinguishing good and poor responding ER2+/HER2+ breast tumors.
Figure 1B:
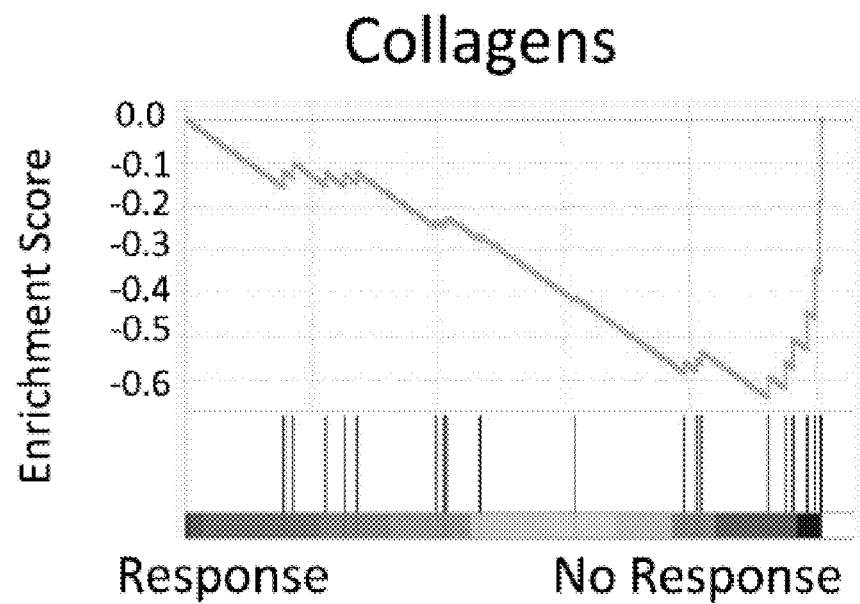
FIG. 1B is a graph from GSEA revealing enrichment of the gene ontology category, collagens, in pCR-resistant ER2+/HER2+ breast tumors. Each black line represents one gene in the collagen gene ontology gene set.
Figure 1C:
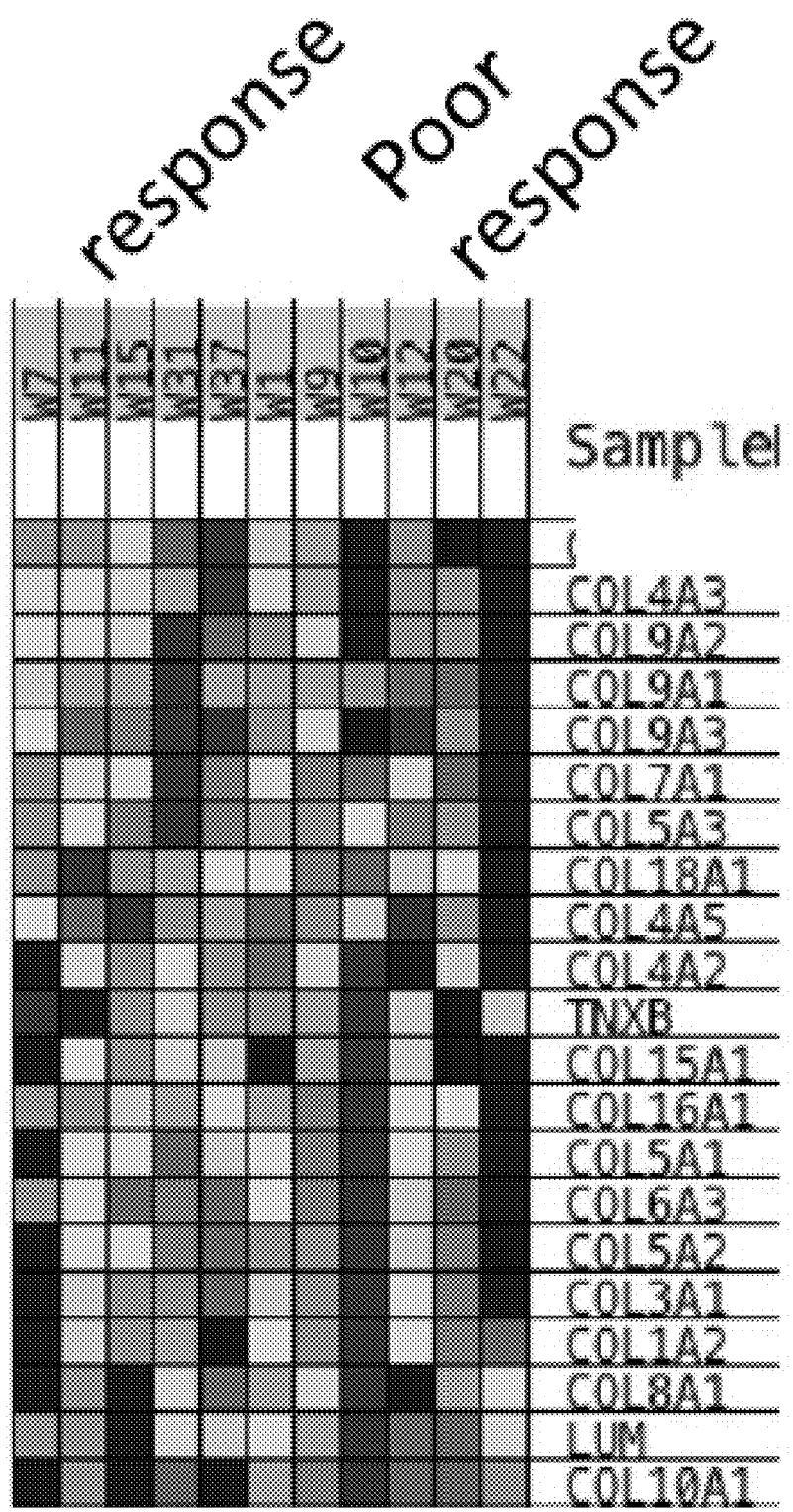
FIG. 1C is a heat map of mRNA expression changes for all measured collagens on a microarray.

Only a fraction of breast cancers respond to adjuvant and neoadjuvant chemotherapy. Standard clinical biomarkers, including ER, HER2, and PR, have been used to identify tumors for specific chemotherapies. Nonetheless, robust biomarkers are needed to better predict subjects who can benefit from adjuvant and neoadjuvant chemotherapy, especially those with ER+/HER2+ breast cancer.

The methods described herein are based, at least in part, on biomarkers that are associated with a pCR to NAC combined with anti-HER2 (NAC+H) or without anti-HER2 therapy. Low expression levels of Col10A1 mRNA and ColXα1 protein predicted pCR independent of other factors (Table 1). Further, a greater abundance of tTILs, lower levels of tumor-associated stroma, and low expression levels of Col3A1 mRNA, ColIIIα1 protein, Col14A1 mRNA, and ColXIVα1 protein are associated with pCR in ER+/HER2+ breast cancer subtypes (Table 1). Thus, measurement of Col10A1 mRNA and/or ColXα1 protein expression with or without a determination of the amount of tTILs, tumor-associated stroma, Col3A1 mRNA, ColIIIα1 protein, Col14A1 mRNA, and/or ColXIVα1 protein will identify subjects most likely to respond to adjuvant chemotherapy, NAC, or NAC+H therapy. This finding defines two classes of ER+/HER2+ breast tumors and define how subjects respond to therapy.

TABLE 1

Biomarkers of Chemotherapy Response

| | | GenBank Accession No. | |
|---|---|---|---|
| Gene | NCBI Human Gene Name | Human Nucleic Acid | Human Amino Acid |
| Col10A1 | collagen type 10 alpha 1 | NM_000493 | NP_000484 |
| Col3A1 | collagen type 3 alpha 1 | NM_000090 | NP_000081, AAH28178 |
| Col14A1 | collagen type 14 alpha 1 | NM_001845, NM_001303110 | NP_000081 |

Genome-wide expression analysis of a set of ER+/HER2+ cases divided the cases into two groups, a group with good response and group with a poor response based on the pathologic evaluation of post-NAC resections. Pathologic complete response is an accepted surrogate as a primary endpoint for response and is associated with long term outcome, however, it has been variably defined (Kaufmann et al., *Journal of Clinical Oncology* 24:1940-1949, 2006). Studies have shown that eradication of tumor from both the breast and axillary lymph nodes (ypT0 pN0 and ypT0/is ypN0) was better associated with improved disease free survival (EFS) and overall survival (OS) than was eradication of invasive tumor from the breast alone (ypT0/is) (Cortazar et al., *Lancet* 384:164-172, 2014). Residual Center Burden (RCB) scoring was used, which considers both primary tumor as well as axillary response. pCR is no residual disease (RCB 0) and minimal residual disease (RCB 1), and those with RCB 2 to 3 are defined as poor responders. Pathway analysis identified collagens and immune pathways as strongly associated with pCR. The collagen transcript, Col10A1, was one of the top-ranked transcripts associated with NAC response for which an available commercial antibody was available. Collagen type 10 alpha 1 (gene name Col10A1 and protein product ColXα1) is a homotrimeric, short-chain collagen and is up-regulated in a variety of tumor types with restricted or undetectable expression in a large spectrum of normal tissues, normal primary cultures and tumor cell lines (Kielty et al., *Biochemical Journal* 227:545-554, 1985; Chapman et al., *Future Oncology* 8:1031-1040, 2012). After validation of the microarray observations by qPCR, the association of ColXα1 protein levels with chemotherapy response was tested by immunohistochemistry. Col10A1 mRNA and ColXα1 protein expression reveal variable signal in the stroma among ER+/HER2+ breast cancers and predicts response to chemotherapy.

Methods of Treating a Subject Having ER+/HER2+ Breast Cancer

Described herein are a variety of methods of treating a subject having ER+/HER2+ breast cancer by detecting, determining, or assaying levels of Col10A1 mRNA and/or ColXα1 protein expression with or without a determination of the amount of tTILs, tumor-associated stroma, Col3A1 mRNA, ColIIIα1 protein, Col14A1 mRNA, and/or ColXIVα1 protein. Such detections are useful, for example, for purposes of diagnosis and treatment. Thus, the methods described herein can include using levels of Col10A1 mRNA, ColXα1 protein, tTILs, tumor-associated stroma, Col3A1 mRNA, ColIIIα1 protein, Col14A1 mRNA, and/or ColXIVα1 protein to select a treatment for a subject with ER+/HER2+ breast cancer and administering an effective amount of adjuvant, NAC, or NAC+H therapy, e.g., docetaxel, carboplatin, doxorubicin, cyclophosphamide, paclitaxel, trastuzumab, pertuzumab, lapatinib, and/or a drug targeted to ColXα1, ColIIIα1, and/or ColXIVα1, e.g., antibody-drug conjugates (ADC) with antibodies to ColXα1, ColIIIα1, and/or ColXIVα1.

The terms "effective amount" and "effective to treat," as used herein, refer to an amount that is effective within the context of its administration for causing an intended effect or physiological outcome. Effective amounts in the present context include, for example, amounts that reduce or shrink a tumor before the main treatment, which can include surgery. Standard treatments for ER+/HER2+ breast cancer include administration of drugs, e.g., docetaxel, carboplatin, doxorubicin, cyclophosphamide, paclitaxel, trastuzumab, pertuzumab, and/or lapatinib.

For example, the methods can include detecting a level of Col10A1 mRNA, ColXα1 protein, tTILs, tumor-associated stroma, Col3A1 mRNA, ColIIIα1 protein, Col14A1 mRNA, and/or ColXIVα1 protein in a sample comprising ER+/HER2+ cancerous breast tissue from a subject, and administering adjuvant chemotherapy, NAC, or NAC+H therapy to the subject if the expression level of collagen type 10 alpha 1 is the same or lower than a collagen type 10 alpha 1 reference level, if the tTILs is the same or greater than a tTILs reference level, if the level of tumor-associated stroma is the same or lower than a tumor-associated stroma reference level, if the expression level of collagen type 3 alpha 1 is the same or lower than a collagen type 3 alpha 1 reference level, and/or if the expression level of collagen type 14 alpha 1 is the same or lower than a collagen type 14 alpha 1 reference level; and administering a treatment that does not comprise adjuvant chemotherapy, NAC, or NAC+H therapy to the subject if the expression level of collagen type 10 alpha 1 is the greater than the collagen type 10 alpha 1 reference level, if the tTILs is lower than the tTILs reference level, if the level of tumor-associated stroma is greater than the tumor-associated stroma reference level, if the expression level of collagen type 3 alpha 1 is greater than the collagen type 3 alpha 1 reference level, and/or if the expression level of collagen type 14 alpha 1 is greater than the collagen type 14 alpha 1 reference level. As explained further below, the reference level can be a preselected reference level or threshold. As one example, the treatment can include administration of adjuvant chemotherapy, NAC, or NAC+H therapy, e.g., docetaxel, carboplatin, doxorubicin, cyclophosphamide, paclitaxel, trastuzumab, pertuzumab, and/or lapatinib.

Detecting Levels of Collagens

The methods described herein can include detecting a level of Col10A1 mRNA, ColXα1 protein, Col3A1 mRNA, ColIIIα1 protein, Col14A1 mRNA, and/or ColXIVα1 protein in a sample from a subject, e.g., a sample comprising ER+/HER2+ cancerous breast tissue. Any method can be used to obtain a sample, such as a biopsy (e.g., core needle biopsy), and the tissue can be embedded in OCT® (Optimal Tissue Cutting compound) for processing. For example, the tissue in OCT® can be processed as frozen sections. Tumor cells can be collected, such as by laser capture microdissection (LCM), and gene expression or protein levels can be assayed using methods known in the art or described herein. In one exemplary approach, the level of Col10A1, Col3A1, and/or Col14A1 mRNA expression is assayed by real-time quantitative RT-PCR. The level of expression of ColXα1, ColIIIα1, and/or ColXIVα1 protein can be determined by immunohistochemistry.

If the levels of Col10A1 mRNA or ColXα1 protein are at or below a reference level, adjuvant chemotherapy, NAC (e.g., docetaxel, carboplatin, doxorubicin, cyclophosphamide, and/or paclitaxel), or NAC+H therapy (e.g., docetaxel, carboplatin, doxorubicin, cyclophosphamide, paclitaxel, trastuzumab, pertuzumab, and/or lapatinib), is appropriate. If levels of Col10A1 mRNA or ColXα1 protein are above a reference level, a treatment that does not comprise adjuvant chemotherapy, NAC, or NAC+H therapy is appropriate.

"Low" and "high" expression levels are relative values and are based on a comparison with those of a respective reference. In one embodiment, a reference level of expression is the expression level of Col10A1 mRNA, ColXα1 protein, Col3A1 mRNA, ColIIIα1 protein, Col14A1 mRNA, or ColXIVα1 protein in a sample cancer population from which Col10A1 mRNA, ColXα1 protein, Col3A1 mRNA, ColIIIα1 protein, Col14A1 mRNA, or ColXIVα1 protein expression data is collected. The expression level in a reference can be determined by measuring gene or protein expression levels in the sample population. In some embodiments, a tumor exhibits "low" Col10A1 mRNA, ColXα1 protein, Col3A1 mRNA, ColIIIα1 protein, Col14A1 mRNA, or ColXIVα1 protein levels if the expression level is the same or less than the mean or median Col10A1 mRNA, ColXα1 protein, Col3A1 mRNA, ColIIIα1 protein, Col14A1 mRNA, or ColXIVα1 protein expression level in a respective reference, and the tumor exhibits "high" Col10A1 mRNA, ColXα1 protein, Col3A1 mRNA, ColIIIα1 protein, Col14A1 mRNA, or ColXIVα1 protein levels if the expression level is above the mean or median Col10A1 mRNA, ColXα1 protein, Col3A1 mRNA, ColIIIα1 protein, Col14A1 mRNA, or ColXIVα1 protein expression level in the respective reference. "Low" and "high" expression levels are relative and can be established with each new reference group. In one alternative, the expression level determined to be predictive of a subject's response to a NAC or NAC+H therapy can be equal to or less than the expression level of the lowest third, or lowest quartile of a reference, or the predictive expression level can be determined to be a level higher than the expression level of the highest third, or highest quartile of a reference.

The samples from a reference can be taken from subjects of the same species (e.g., human subjects), and the tumors of a reference are preferably of the same type (e.g., ER+/HER2+ breast tumors). In some embodiments, the tumors of a reference can all be, for example, from an ER+/HER2+ breast tumor. The individual members of a reference may also share other similarities, such as similarities in stage of disease, previous treatment regimens, lifestyle (e.g., smokers or nonsmokers, overweight or underweight), or other demographics (e.g., age, genetic disposition). For example, besides having the same type of tumor, subjects in a reference may not have received any previous chemotherapy. A reference level should include gene expression analysis data from tumor samples from at least 2, 3, 5, 8, 10, 15, 20, 25, 30, 40, 50, 60, 70, 80, 90, 100, 120, 140, 160, 180, or 200 subjects. In some embodiments, the reference level is taken from non-tumorous tissue of the subject, e.g., normal tissues, preferably of the same tissue type (e.g., normal breast tissue).

Gene expression levels in a sample or reference can be determined by any method known in the art. Expression levels in a tumor sample from a test subject are determined in the same manner as expression levels in the reference. For example, the level of a Col10A1, Col3A1, and/or Col14A1 mRNA (transcript) can be evaluated using methods known in the art, e.g., Northern blot, RNA in situ hybridization (RNA-ISH), RNA expression assays, e.g., microarray analysis, RT-PCR, deep sequencing, cloning, branched DNA assays, and real-time quantitative polymerase chain reaction (RT-qPCR). Analytical techniques to determine RNA expression are known. See, e.g., Sambrook et al., *Molecular Cloning: A Laboratory Manual*, 3rd Ed., Cold Spring Harbor Press, Cold Spring Harbor, N.Y. (2001).

In some embodiments, the methods include using a branched-chain DNA assay to directly detect and evaluate the level of Col10A1, Col3A1, and/or Col14A1 mRNA in the sample (see, e.g., Luo et al., U.S. Pat. No. 7,803,541; Canales et al., *Nature Biotechnol* 24:1115-1122, 2006). In some embodiments, the methods include analysis of the DNA with nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with different codes for each of the biomarkers to be quantified or detected, allowing for highly multiplexed analysis (Geiss et al., *Nat Biotechnol* 26:317-25, 2008).

In some embodiments, the level of ColXα1, ColIIIα1, and/or ColXIVα1 protein is detected. The presence and/or level of a protein can be evaluated using methods known in the art, e.g., using quantitative immunoassay methods such as enzyme linked immunosorbant assays (ELISAs), immunoprecipitations, immunofluorescence, immunohistochemistry, enzyme immunoassay (EIA), radioimmunoassay (RIA), diagnostic magnetic resonance, and Western blot analysis. In some embodiments, the methods include contacting an agent that selectively binds to ColXα1, ColIIIα1, and/or ColXIVα1 protein (such as an antibody or antigen-binding portion thereof) with a sample, to evaluate the level of protein in the sample. In some embodiments, the antibody bears a detectable label. Antibodies can be polyclonal, or more preferably, monoclonal. An intact antibody, or an antigen-binding fragment thereof (e.g., Fab or F(ab')2) can be used. The term "labeled," with regard to an antibody encompasses direct labeling of the antibody by coupling (i.e., physically linking) a detectable substance to the antibody, as well as indirect labeling of the antibody by reactivity with a detectable substance. Examples of detectable substances are known in the art and include chemiluminescent, fluorescent, radioactive, or colorimetric labels. For example, detectable substances can include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

In some embodiments, microfluidic (e.g., "lab-on-a-chip," "micro-a-fluidic chips") devices can be used in the present methods for detection and quantification of ColXα1, ColIIIα1, and/or ColXIVα1 protein in a sample. Such devices have been successfully used for microfluidic flow cytometry, continuous size-based separation, and chromatographic separation. In particular, such devices can be used for the isolation of specific biological particles such as specific proteins (e.g., ColXα1, ColIIIα1, and/or ColXIVα1) from tissue samples. A variety of approaches may be used to separate ColXα1, ColIIIα1, and/or ColXIVα1 proteins from a heterogeneous sample. For example, some techniques can use functionalized materials to capture ColXα1, ColIIIα1, and/or ColXIVα1 using functionalized surfaces that bind to the target cell population. The functionalized materials can include surface-bound capture moieties such as antibodies or other specific binding molecules, such as aptamers, as are known in the art. Accordingly, such microfluidic chip technology may be used in diagnostic and prognostic devices for use in the methods described herein. For examples, see, e.g., Lion et al., Electrophoresis 24 21 3533-3562, 2003; Fortier et al., *Anal Chem* 77:1631-1640, 2005; US 2009/0082552; and U.S. Pat. No. 7,611,834. Also included in the present application are microfluidic devices comprising ColXα1, ColIIIα1, and/or ColXIVα1 binding moieties, e.g., anti-ColXα1, anti-ColIIIα1, and/or anti-ColXIVα1 antibodies or antigen-binding fragments thereof.

In some embodiments, high throughput methods, e.g., protein or gene chips as are known in the art (see, e.g., Ch. 12, "Genomics," in Griffiths et al., Eds. *Modern Genetic Analysis*, 1999, W. H. Freeman and Company; Ekins and Chu, Trends in Biotechnology, 1999; 17:217-218; MacBeath and Schreiber, Science 289:1760-1763, 2000; Simpson, *Pro-* teins and Proteomics: A Laboratory Manual, Cold Spring Harbor Laboratory Press; 2002; Hardiman, *Microarrays Methods and Applications: Nuts & Bolts*, DNA Press, 2003), can be used to detect the presence and/or level of Col10A1 mRNA, ColXα1 protein, Col3A1 mRNA, ColIIIα1 protein, Col14A1 mRNA, and/or ColXIVα1 protein.

The tumor can be sampled for expression levels of Col10A1 mRNA, ColXα1 protein, Col3A1 mRNA, ColIIIα1 protein, Col14A1 mRNA, and/or ColXIVα1 protein, and an appropriate chemotherapy can be selected based on the observed expression levels. The chemotherapy can include a single agent or multiple chemotherapeutic agents (e.g., two, three, or more chemotherapeutic agents). For example, when expression levels of Col10A1 mRNA, ColXα1 protein, Col3A1 mRNA, ColIIIα1 protein, Col14A1 mRNA, and/or ColXIVα1 protein are determined to be the same or lower compared to a respective reference level, an appropriate adjuvant chemotherapy, NAC, or NAC+H therapy can be selected, prescribed, and/or administered. When expression levels of Col10A1 mRNA, ColXα1 protein, Col3A1 mRNA, ColIIIα1 protein, Col14A1 mRNA, and/or ColXIVα1 protein are determined to be higher compared to a respective reference level, an appropriate treatment that does not comprise adjuvant chemotherapy, NAC, a NAC+H therapy can be selected, prescribed, and/or administered.

Chemotherapy can be administered by standard methods, including orally, such as in the form of a pill, intravenously, by injection into a body cavity (such as the bladder), intraperitoneally, intramuscularly, or intrathecally. A chemotherapy regimen can be delivered as a continuous regimen, e.g., intravenously, orally, or in a body cavity. A chemotherapy regimen can be delivered in a cycle including the day or days the drug is administered followed by a rest and recovery period. The recovery period can last for one, two, three, or four weeks or more, and then the cycle can be repeated. A course of chemotherapy can include at least two to 12 cycles (e.g., three, four, five, six, seven, ten or twelve cycles).

Gene expression data obtained from the methods featured herein can be combined with information from a patient's medical records, including demographic data; vital status; education; history of alcohol, tobacco and drug abuse; medical history; and documented treatment to adjust conclusions relating to the prognosis of a proliferative disorder following administration of a chemotherapy designed as described above.

Detecting Levels of tTILs and Tumor-Associated Stroma

The amount of tTILs and tumor-associated peri- and intra-tumoral stroma can be detected or determined by routine procedures in the art, e.g., morphologically evaluated in relation to response on pre-treated biopsy samples using, for example, samples of 2-5 needle cores of average 1.5 cm in length obtained by a 12 gauged needle. The amount of tumor-associated stroma can be scored from 0 to 2: "0" for 10% for absent or minimal intratumoral stroma, "1" for mild to moderate amount of intratumoral stroma 10-40%, and "2" for ≥40% intratumoral stroma. Prominent stroma can be defined as abundant intratumoral stroma tissue volume with a score of "2" (≥40%) on a biopsy sample. The stroma and intratumoral TIL scores can be evaluated based on criteria published by Adams et al. (*Journal of Clinical Oncology*, 2014, doi: 10.1200/JCO.2013.55.0491. PubMed PMID: 25071121).

ColXα1, ColIIIα1, and ColXIVα1 Targeted Drugs and Treatments

Particularly useful in the presently described methods are drugs targeted to ColXα1, ColIIIα1, and ColXIVα1. For example, the ColXα1, ColIIIα1, and ColXIVα1-target drug can be an antibody-drug conjugate, e.g., a cytotoxic drug covalently linked to a monoclonal antibody directed to an antigen that is differentially overexpressed in tumor cells. These loaded antibodies can selectively deliver lethal drugs to tumor cells and provide sustained clinical benefit to pre-selected cancer patients while, at the same time, minimizing systemic toxicity. See, e.g., Sievers et al., *Annu Rev Med* 64:15-29, 2013; Bouchard et al., *Bioorg Med Chem Lett* 24:5357-5363, 2014.

In one aspect, the present disclosure provides methods of treating a subject diagnosed as having ER+/HER2+ breast cancer, wherein an expression level of ColXα1, ColIIIα1, and/or ColXIVα1 is detected, determined, or assayed from a sample of cancerous breast tissue from the subject. The expression level of ColXα1, ColIIIα1, and/or ColXIVα1 can be detected by immunohistochemistry, as described herein. If the expression level of ColXα1 is greater than a ColXα1 reference level, the subject can be administered a drug targeted to ColXα1, e.g., an anti-ColXα1 antibody conjugated to the drug; and administering to the subject a treatment that does not include a drug targeted to ColXα1 if the expression level of ColXα1 is the same or lower than the ColXα1 reference level. If the expression level of ColIIIα1 is greater than a ColIIIα1 reference level, the subject can be administered a drug targeted to ColIIIα1, e.g., an anti-ColIIIα1 antibody conjugated to the drug; and administering to the subject a treatment that does not include a drug targeted to ColIIIα1 if the expression level of ColIIIα1 is the same or lower than the ColIIIα1 reference level. If the expression level of ColXIVα1 is greater than a ColXIVα1 reference level, the subject can be administered a drug targeted to ColXIVα1, e.g., an anti-ColXIVα1 antibody conjugated to the drug; and administering to the subject a treatment that does not include a drug targeted to ColXIVα1 if the expression level of ColXIVα1 is the same or lower than the ColXIVα1 reference level. In any of the methods described herein, the treatment may in some instances not comprise an antibody-drug conjugate with anti-ColXα1 antibody, anti-ColIIIα1 antibody, or anti-ColXIVα1 antibody if the expression level of ColXα1, ColIIIα1, or ColXIVα1 is the same or lower than its respective reference level. To produce antibodies bound to various drugs, e.g., calicheamicin-, auristatin-, and/or maytansine-based cytotoxic drugs, conventional techniques known to skilled practitioners can be used. See, e.g., Sievers et al., *Annu Rev Med* 64:15-29, 2013; Bouchard et al., *Bioorg Med Chem Lett* 24:5357-5363, 2014.

Antibodies to ColXα1, ColIIIα1, and ColXIVα1 are known in the art and also commercially available. Further, methods for producing antibodies are well known to skilled practitioners. Antibodies used in the present invention may include monoclonal antibodies, polyclonal antibodies, humanized or chimeric antibodies, single chain antibodies, Fab fragments, F(ab')$_2$ fragments, and molecules produced using a Fab expression library.

As used herein, the term "antibody" refers to a protein comprising at least one, e.g., two, heavy (H) chain variable regions (abbreviated herein as VH), and at least one, e.g., two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat et al., *Sequences of Proteins of Immunological Interest, Fifth Edition*, U.S. Department of Health and Human Services, *NIH* Publication No. 91-3242, 1991; and Chothia et al., *J. Mol. Biol.* 196:901-917, 1987). Each VH and VL is composed of three CDRs and four FRs, arranged from amino-terminus to carboxy-terminus in the following order: FR1, CDR1, FR2, CDR2, FR3, CDR3, and FR4.

A ColXα1-, ColIIIα1-, or ColXIVα1-binding fragment of an antibody refers to one or more fragments of a full-length antibody that retain the ability to specifically bind to a ColXα1, ColIIIα1, or ColXIVα1 polypeptide, respectively, or to portions thereof. Examples of polypeptide binding fragments of an antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated CDR.

Subjects to be Treated

A subject can be selected on the basis that they have, or are at risk of developing, ER+/HER2+ breast cancer. It is well within the skills of an ordinary practitioner to recognize a subject who has, or is at risk of developing, ER+/HER2+ breast cancer. A subject who has, or is at risk of developing, ER+/HER2+ breast cancer is one having one or more symptoms of the condition or one or more risk factors for developing the condition. Symptoms of ER+/HER2+ breast cancer are known to those of skill in the art and include, without limitation, new lump(s) in the breast or underarm (armpit), thickening or swelling of part of the breast, irritation or dimpling of breast skin, redness or flaky skin in the nipple area or the breast, pulling in of the nipple or pain in the nipple area, nipple discharge other than breast milk, any change in the size or the shape of the breast, and pain in any area of the breast. A subject who has, or is at risk of developing, ER+/HER2+ breast cancer is one with known risk factors such as inherited changes in the BRCA1 or BRCA2 genes or in other genes that increase the risk of breast cancer, long-term use of hormone replacement therapy, personal history of breast cancer or non-cancerous breast diseases, family history of breast cancer, treatment with radiation therapy to the breast/chest, exposure to diethylstilbestrol, dense breasts by mammogram, alcohol consumption, and night-shift work. The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, and horses.

The invention is further described in the following examples, which do not limit the scope of the invention described in the claims.

EXAMPLES

Patients and Tissue Samples 538 patients with invasive breast cancer treated at Lifespan Medical Center and Women and Infant's Hospital during the period of 2007-2014 who received NAC were retrospectively identified. This cohort included 74 ER+/HER2+ breast cancer subtypes were identified that had tissue available. Most of the patients had clinical stage T2 or T3 tumors prior to NAC (Table 2). Histological features such as tumor type, size, extent of the disease, lymph node status, and histological grade using the Nottingham combined histologic grading system was reviewed. Immunohistochemistry of ER, HER2, and PR expression were classified according to the CAP/ASCO guidelines (Hammond et al., *Archives of Pathology & Laboratory Medicine* 134:907-922, 2010). Pathological response to NAC was assessed by the AJCC cancer staging and residual cancer burden (RCB) score (Sahoo, *Archives of Pathology & Laboratory Medicine* 133:633-642, 2009). This RCB system uses size of residual carcinoma, cellularity distributed over the tumor bed, the number of lymph nodes with metastases, and the size of the largest metastasis into a continuous index to define four RCB categories (0, 1, 2, and 3) associated with increasing risk of recurrence, as described on the world wide web at mdanderson.org/breastcancer_RCB.

TABLE 2

Association of clinical characteristics to neoadjuvant pCR by subtype. P was calculated by Fisher exact test.

| Characteristic | No. | % pCR | P |
|---|---|---|---|
| ER2+/HER2+ cases used for Collagen X IHC | | | |
| No. of patients | 50 | 36 | |
| Residual Cancer Burden | | | |
| 0 | 8 | | |
| 1 | 10 | | |
| 2 | 6 | | |
| 3 | 26 | | |
| Age, y | | | 0.006 |
| <50 | 18 | 62 | |
| ≥50 | 32 | 28 | |
| Pre-Treatment Lymph Node Status | | | 0.3 |
| Negative | 15 | 47 | |
| Positive | 35 | 31 | |
| Pre-Treatment Tumor Stage | | | 0.8 |
| T1c/T2 | 35 | 37 | |
| T3/T4 | 15 | 33 | |
| Tumor Grade | | | 0.35 |
| 2 | 21 | 28.6 | |
| 3 | 29 | 41.4 | |
| colXα1 | | | 0.000* |
| 0 | 9 | 87.5 | |
| 1 | 17 | 58.8 | |
| 2 | 9 | 0 | |
| 3 | 15 | 0 | |
| sTIL | | | 0.007* |
| 0 ≤ 10% | 20 | 15 | |
| 11 ≤ 20% | 9 | 22 | |
| 21 ≤ 30% | 5 | 40 | |
| 31 ≤ 40% | 7 | 42 | |
| 41 ≤ 50% | 7 | 86 | |
| 51 ≤ 60% | 2 | 100 | |
| >60% | 0 | | |
| Stroma | | | 0.005* |
| 0 | 2 | 100 | |
| 1 | 23 | 52 | |
| 2 | 25 | 16 | |
| All ER2+/Her2+ Cases | | | |
| No. of patients | 74 | 41 | |
| Residual Cancer Burden | | | N/A |
| 0 | 14 | | |
| I | 16 | | |
| II | 11 | | |
| III | 33 | | |
| Age, y | | | 0.07 |
| <50 | 35 | 51 | |
| ≥50 | 39 | 31 | |
| Pre-Treatment Lymph Node Status | | | 0.47 |
| Negative | 26 | 46 | |
| Positive | 48 | 38 | |

TABLE 2-continued

Association of clinical characteristics to neoadjuvant
pCR by subtype. P was calculated by Fisher exact test.

| Characteristic | No. | % pCR | P |
|---|---|---|---|
| Tumor Grade | | | 0.33 |
| 2 | 25 | 32 | |
| 3 | 49 | 45 | |
| Pre-Treatment Tumor Stage | | | 0.09 |
| T1c/T2 | 51 | 47 | |
| T3/T4 | 23 | 26 | |
| sTIL | | | 0.000* |
| 0 ≤ 10% | 27 | 11 | |
| 11 ≤ 20% | 15 | 40 | |
| 21 ≤ 30% | 8 | 37.5 | |
| 31 ≤ 40% | 10 | 60 | |
| 41 ≤ 50% | 12 | 83 | |
| 51 ≤ 60% | 2 | 100 | |
| >60% | 0 | | |
| Stroma | | | 0.000* |
| 0 | 6 | 100 | |
| 1 | 39 | 51.3 | |
| 2 | 29 | 14.0 | |

*Pearson Chi-Square p-value

Microarray and qPCR Analysis

RNA Extraction and Purification

From the ER+/HER2+ patients, a mixture of good and poor responders were selected for whom there was sufficient tissue for this assay. Ten 10 μm tumor sections were scraped from the slides for total RNA extraction. RNA was purified using the RecoverAll Total Nucleic Acid Extraction Kits for FFPE tissues (Ambion, Austin, Tex.) and further purified and concentrated with the RNeasy Minelute Cleanup Kit (Qiagen, Valencia, Calif.).

Expression Microarray and qPCR

RNA was isolated and purified using the RNeasy FFPE kit (Qiagen, Valencia, Calif.) from 11 cases. 100 ng of total RNA was amplified using Affymetrix's Sensation Plus FFPE amplification kit following the manufacturer's instructions and labeled cDNA was hybridized to Affymetrix (Santa Clara, Calif.) HTA 2.0 microarrays and visualized at the Brown University Genomics Core Facility following the manufacturer's instructions. Signals were estimated using RMA (Irizarry et al., *Biostatistics* 4:249-264, 2003). Fold change, t-tests, and multiple hypothesis tests were calculated in R. Data are available in GEO, GSE67982.

For real-time qPCR, cDNA was prepared using Quanti-Tect Reverse Transcription Kit (Qiagen). qPCR was performed on a Mx3005p (Agilent) with Brilliant III SYBR Green (Agilent). Relative expression fold changes were calculated relative to GAPDH by the $\Delta C_t$ method.

Gene Expression and Pathway Analysis

Microarray signals were analyzed for statistical significance in terms of differences between samples between good and poor responders. We applied gene set enrichment analysis (GSEA) to investigate pathways and groups of genes that may be associated with NAC response, which identified collagens and immune pathways as strongly associated with good pathologic response. The collagen transcript, Col10A1, was one of the top-ranked transcripts associated with NAC response for which an available commercial antibody was available. After verification of the microarray observations by qPCR, the association of ColXα1 expression was tested as well as other tumor microenvironmental factors such as the abundance of tumor associated stroma and tTILs in the pre-treatment biopsy samples to correlate with post-treatment response. TCGA RNA-seq data for breast invasive carcinoma were downloaded from the Firehose Broad GDAC (Broad Institute TCGA Genome Data Analysis Center, 2015). TCGA clinical data were downloaded from the TCGA data archive in September 2015 (cancergenome.nih.gov).

Tumor-Associated Stroma and TIL Analysis

The amount of tumor-associated peri- and intra-tumoral stroma and tTILs was morphologically evaluated in relation to response on pre-treated biopsy samples, which commonly were samples of 2-5 needle cores of average 1.5 cm in length obtained with either a 14 gauge spring-loaded biopsy device or a 12 gauge vacuum-assisted biopsy device. The amount of tumor-associated stroma is scored as 0 to 2: "0" for 10% for absent or minimal intratumoral stroma, "1" for mild to moderate amount of intratumoral stroma 10-40%, and "2" for abundant (≥40%) stroma. Stromal and intratumoral TILs (sTILs and iTILs) were evaluated based on criteria published by Denkert et al. (*J Clinical Oncol* 28:105-113, 2010). Briefly, iTILs were defined as lymphocytes in direct contact with the tumor cells, whereas sTILs were defined as lymphocytes in the surrounding stroma, with the percent of the tumor or stromal volume comprised of infiltrating lymphocytes, as opposed to tumor or other stromal tissues, on an H&E stained biopsy section estimated by the reading pathologists, with results reported in increments of 10 (0-1% was scored as 0, with all other estimates rounded up to the next highest decile—i.e., 11-20% was scored as 20). sTILs and iTILs were totaled to calculate tTILs. The trends were similar for each lymphocyte fraction. sTILs were chosen to be analyzed as they were considered to the most consistent metric as recommended by the International TILs Working Group (Salgado et al., *Ann Oncol* 26(2):259-271, 2015). The histological evaluation was graded independently by two pathologists, who were blinded to clinical information including the post-treatment outcome, at the time of analysis, with the summary score representing the mean of the two separate scores. The two pathologists evaluated 30 separate cases (triple negative breast cancer cases) together to get a general agreement of the sTIL. The actual study cases were evaluated independently, the concordance is about 95%. The cases with greater than 10% difference were reviewed together and the average score was used.

Immunohistochemistry and ColXα1 Scoring

Four-micron sections were cut from formalin-fixed paraffin-embedded tissue blocks, heated at 60° C. for 30 minutes, deparaffinized, rehydrated, and subjected to antigen retrieval by heating the slides in epitope retrieval buffer in a water bath at 95° C. for 45 minutes. The slides were then incubated with either mouse monoclonal antibodies or rabbit polyclonal antibodies for 30 minutes at room temperature in a DAKO Autostainer. Anti-ColXα1 (1:50, eBioscience/Affymetrix, Clone X53), estrogen receptor (1:50, DAKO (Santa Clara, Calif., USA), clone 1D5), progesterone receptor (1:400, DAKO, clone 1A6), and HER2/neu (DAKO HERCEPTEST™) were used for immunohistochemistry. The immunoreactivity was detected using the DAKO EnVision method according to the manufacturers recommended protocol. Peri- and intra-tumoral stromal staining for ColXα1 was scored as 0, 1+, 2+, and 3+. Briefly, 0 as no staining; 1+ as weak staining; 2+ as <10% of stroma tissue with intense staining present; 3+ as >10% of stroma tissue with patchy intense staining. All scoring was performed blinded to the outcome and many cases were scored before the outcome data was available.

Statistical Analysis

SPSS v22 for MacOS (SPSS, Chicago, Ill., USA) was used for all statistical analyses. P<0.05 was considered statistically significant. All p-values reported are two-sided.

For the logistic regression, all factors were analyzed as continuous variables.

Results

Clinical Information

Clinical and pathologic information of the study group is summarized in Table 2. In this group of 74 ER+/HER2+ breast cancer patients, 92% had clinical stage≥IIB (68 of 74). Two common adjuvant and neoadjuvant chemotherapy regimens docetaxel/carboplatin/trastuzumab (TCH)) and doxorubicin, cyclophosphamide, paclitaxel, trastuzumab (AC-TH) were used in 68 of the 74 patients (90%). Thirty five patients received TCH regimen, and 33 patients received AC-TH regimen. The addition of pertuzumab to the neoadjuvant regimen for HER2+ cancer had not yet been routinely adopted. 19% (14 of 74) of patients achieved a complete pCR (RCB class 0), and 40.54% (30 of 74) had a good pathologic response (RCB class 0 or I). There were no significant statistical differences in the post-treatment response between patients who received TCH vs. AC-TH treatment options.

Association of Col10A1 mRNA and pCR in ER+/HER2+ Cancer

To identify novel markers of pCR in this subtype, five tumors were randomly selected from patients who achieved good response (RCB 0 or I) with NAC+H and six from patients who did not achieve a good response (RCB II or III) for genome-wide expression profiling using Affymetrix HTA 2.0 microarrays. Even with a small set of cases, candidate markers strongly associated with pCR could be detected (FIG. 1). Only 30 transcripts were significantly differentially expressed (Fc>2, p<0.05) including three collagens (subtypes Col10A1, Col14A1, and Col3A1), which were up-regulated in tumors that had poor response. Other differentially expressed genes associated with more aggressive breast cancer, including ERBB4 and TGFB3, are up-regulated in poor responders in these data. However, qPCR analysis of TGFB3 in 42 tumors did not find a strong association with response (Kolacinska et al., *Mol Biol Rep* 39(7):7435-7441, 2012). Likely because of the small number of significantly differentially expressed transcripts, no transcripts had a corrected p<0.05 after multiple hypothesis correction. Because so few genes were considered significantly differentially expressed, representative significantly differentially expressed genes were verified by qPCR.

Pathway analysis was performed to identify groups of genes associated with good response. GSEA identified many pathways significantly biased towards either good responders or resistant tumors. In ER+/HER2+ tumors, within the Gene Ontology gene sets, increased expression of immune pathways, and components of the cell cycle were associated with pCR, while drug metabolism, RNA metabolism, and expression of certain collagens were associated with poor responding tumors.

Figure 1D:
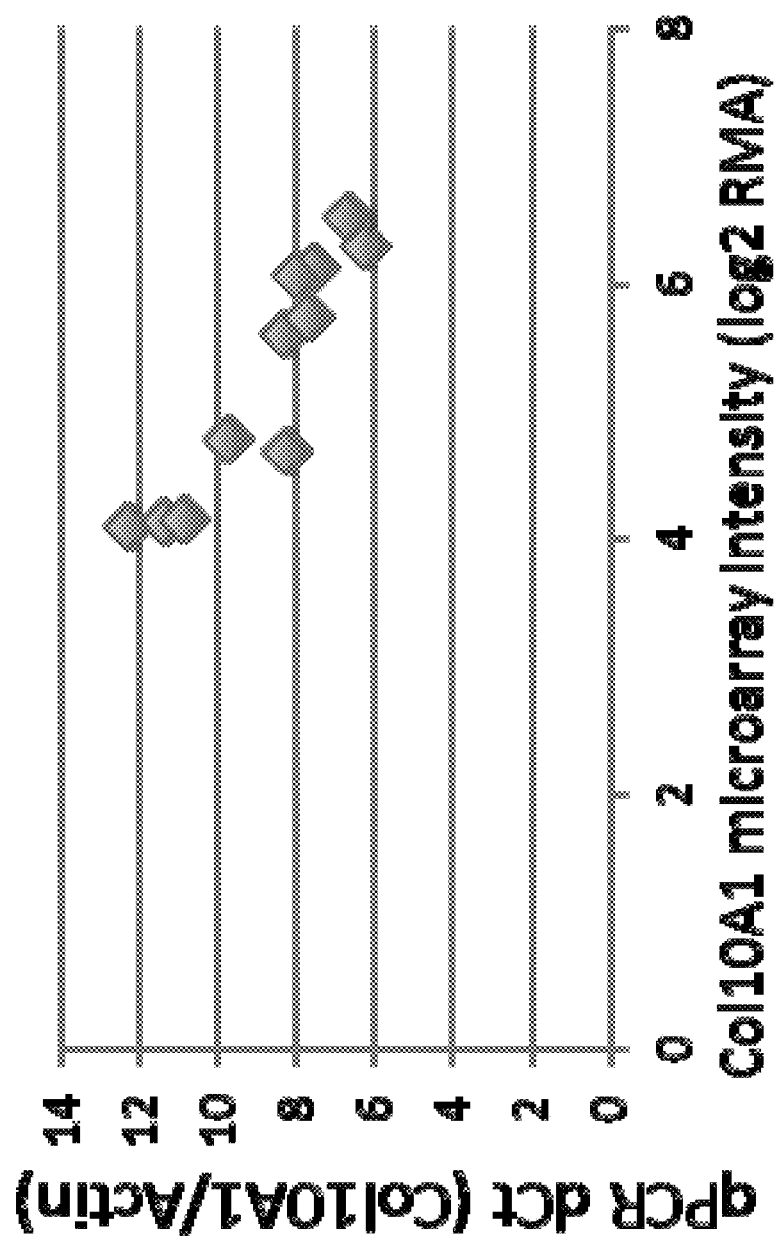
FIG. 1D is a line graph showing qPCR of Col10A1 mRNA expression correlation with microarray results.

The collagen Gene Ontology gene set is strongly biased towards poor responding tumors (NES=-1.9, FDR=0.009) (FIG. 1C), and three transcripts encoding collagens (Col10A1, Col14A1, and Col3A1) were among the most significant differentially expressed genes. To validate the microarray observations, qPCR was performed on five transcripts, significantly differentially expressed (Fc>2, p<0.05) between responding and non-responding tumors among those analyzed by microarrays and found good overall correlation (R=0.69, P<0.001), including the Col10A1 transcript (FIG. 1D).

Total Tumor-Infiltrating Lymphocytes and Tumor-Associated Stroma are Associated with Good Response in ER+/HER2+ Tumors The gene expression data suggested that higher levels of lymphocytes were associated with achieving a good (i.e., pCR) response. This is highlighted by increased expression of CXCL10 (Fc 1.8, p=0.01) and IL7R, highly ranked by GSEA, in responsive tumors. These gene expression data predicted that examination of infiltrating lymphocytes is warranted and that such TILs would be associated with achieving good response.

To test the gene expression observations, each tumor was examined for the number of TILs. TILs have been proposed as a predictor of pCR in triple negative breast cancer (Andre et al., *Clin Cancer Res* 19(1):28-33, 2013). However, the association between TILs and good responders in ER+/HER2+ tumors remains uncertain. Higher levels of TILs corresponded to tumors with good responders in the full 74 ER+/HER2+ patient cohort (Table 2). In univariate analysis using a logistic regression model, TILs were found to be predictive for good response (OR=0.94, P=0.001) (Table 3), and the association with good response was observed for both tumor-associated stroma and TILs (Table 2).

TABLE 3

Odds of response after neoadjuvant chemotherapy from logistic regression model. N = 50.

| Characteristic | OR (95% CI) | P |
|---|---|---|
| Univariate | | |
| Age | 5.6 (1.6-20.0) | 0.008 |
| sTIL | 0.46 (0.29-0.72) | 0.001 |
| Stroma | 6.6 (1.9-23.4) | 0.003 |
| colXα1 | 18.9 (2.8-129) | 0.003 |
| Multivariate | | |
| Age | 0.23 (0.009-50) | 0.37 |
| sTIL | 0.39 (0.16-0.92) | 0.03 |
| Stroma | 1.9 (0.17-22) | 0.6 |
| colXα1 | 28 (1.6-487) | 0.022 |

ColXα1 Expression Predicts Response to NAC in ER+/HER2+ Cancer

The usefulness of an anti-ColXα1 monoclonal antibody to predict pCR was tested, and its relationship with other microenvironment metrics, including the amount of tumor-associated stroma and tTILs, was evaluated for its role in pCR. Immunohistochemistry was performed in 10 reduction mammaplasty cases to define the ColXα1 expression in normal breast tissue. Among the 74 ER+/HER2+ cases in the study group, 50 pre-treatment needle biopsy samples had sufficient material (at least 1 cm tumor/stroma in a 12 gauge needle core) for anti-ColXα1 IHC. The overall response rate (pCR+RCB I) in this set was 36% (18 of 50 patients). Subjects who achieved pCR were significantly more likely to be greater than 50 years old (P=0.018) and have positive lymph nodes (P=0.001). Microenvironmental factors including decreased amount of stroma (P=0.016) and higher levels of tTIL (P<0.001) were associated with patients achieving pCR (Table 2).

Figure 2A:
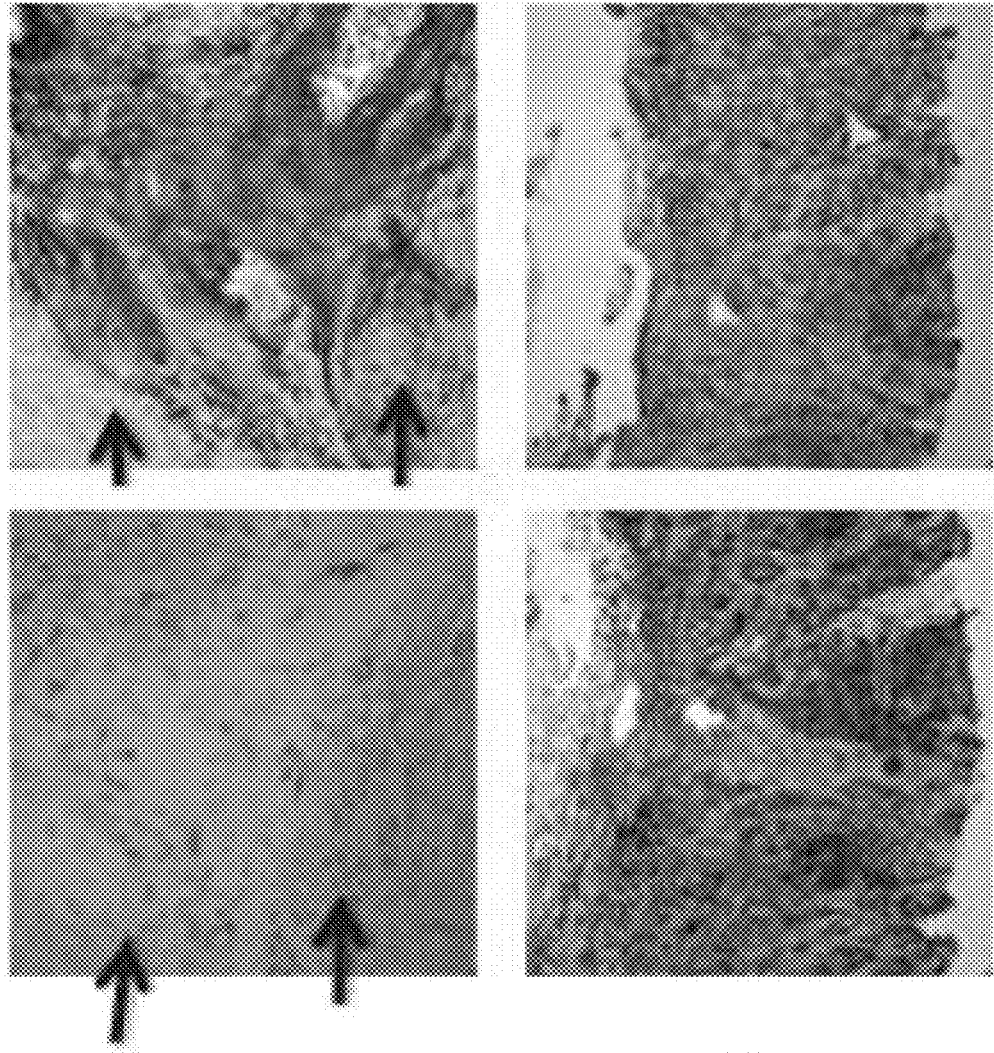
FIG. 2A is a series of four photomicrographs showing ColXα1 immunostaining in low- and high-ColXα1 expressing ER+/HER2+ breast cancers. Two representative cases, one with no response (RCB III) and strong ColXα1 signal, score=2, and one with good response (pCR, RCB 0) and no ColXα1 signal, score=0, are shown. Arrows indicate regions with tumor cells.
Figure 2B:
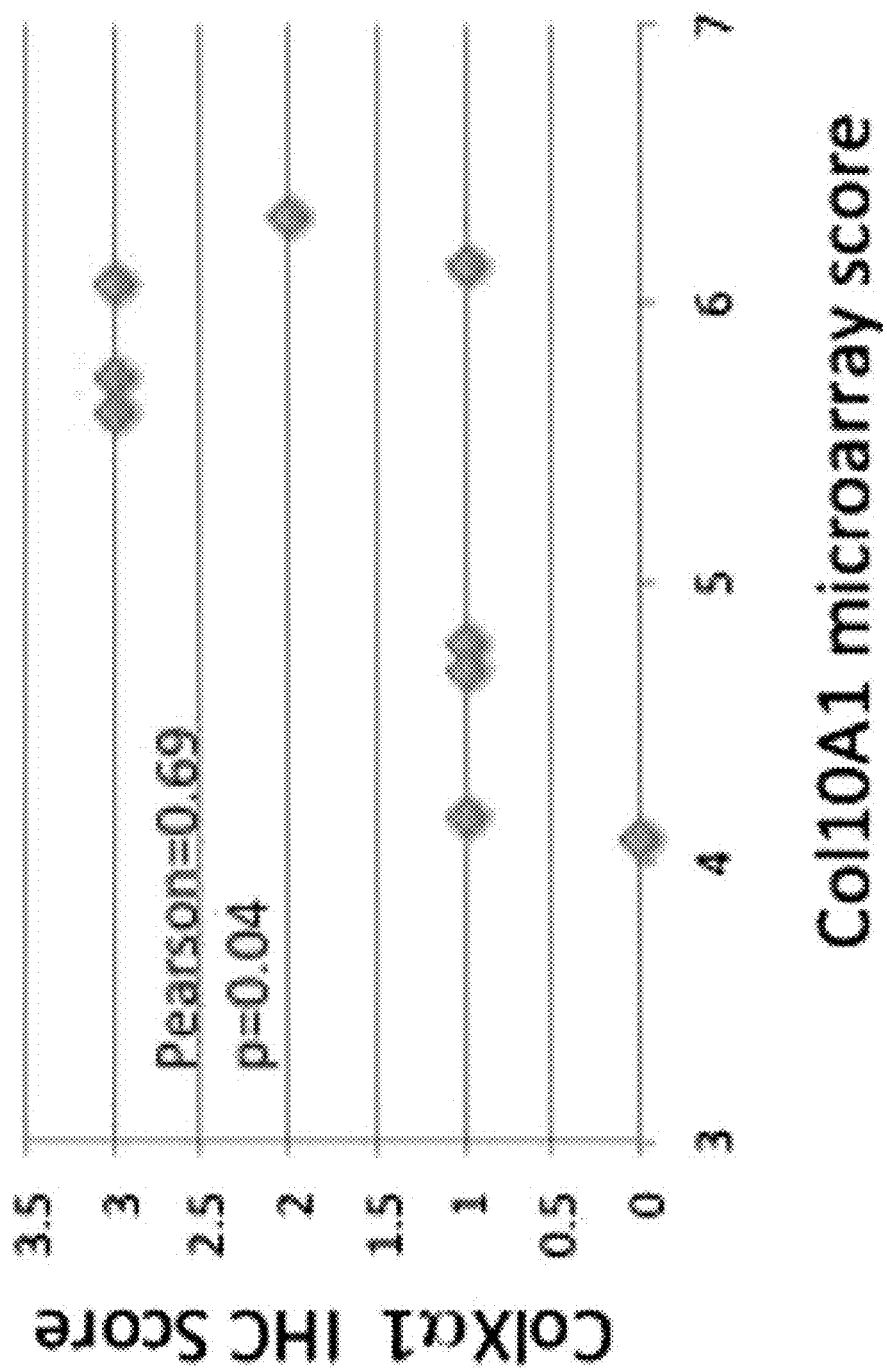
FIG. 2B is a graph showing correlation between Col10A1 mRNA levels, as determined by qPCR, and ColXα1 IHC signal in nine cases.

In tumor samples, immunostaining of colXα1 was observed as intense peri- and intra-tumoral distribution in some tumors in the RCB III case. A periductal/perivascular colXα1 staining pattern was frequently observed (FIG. 2A). Increased colXα1 staining was strongly associated with a poor response by a chi-squared test (P<0.001) (Table 2). The two cases with no stroma were scored as having negative colXα1 staining as no signal was observed.

ColXα1 Predicts NAC Response in ER+/HER2+ Cancer Independently

Univariate and multivariate analyses was performed using a logistic regression model in order to assess the associations between response, TILs, colXα1 IHC, and other established clinicopathological parameters. Univariate analysis showed that high levels of colXα1 measured by IHC were associated with patients not achieving pCR or RCB I (OR=18.88, P=0.003) (Table 3). No patients with tumors with colXα1 scores of 2 or 3 achieved pCR or RCB I. More abundant stroma (OR=6.92, P=0.003) and positive lymph nodes (OR=12.3, P=0.003) were also associated with patients not achieving pCR or RCB I. In contrast, higher levels of TILs were associated with patients achieving good response (OR=0.94, P=0.001). Multivariate analysis was performed comparing two variables at a time to avoid overfitting (Table 3).

Multiple lines of evidence suggest that colXα1 IHC is a strong candidate marker. ColXα1 IHC discriminates good from poor responding patients with a low false positive rate. This is also reflected in the ROC curves where the colXα1 IHC is a more specific and sensitive marker of good response compared to stroma (FIG. 3A). ROC curves and box plots demonstrate that colXα1 and TIL strongly separate patients by good response, while the stroma score did not (FIG. 3). This indicated that high colXα1 expression by itself is an independent predictive factor, and not merely a reflection of more tumor associated stroma. Clinical biomarkers need to have very high specificity and sensitivity (Drucker et al., *EPMA J* 4(1):7, 2013). The high sensitivity, specificity, and accuracy of the colXα1 scoring support its use as a marker for response in the NAC setting.

To further test if ColXα1 contributed significantly compared to histological analysis of stroma, multivariate analysis was performed using a logistic regression model for the parameters with predictive power in the univariate analysis. Nodal status did not contribute significantly with any other parameter. Stroma was a significant predictor when tested with TIL and nodal status, but not with ColXα1 IHC. Notably, ColXα1 IHC was an independent predictor of pCR compared with all other parameters.

Total-Infiltrating Lymphocytes are Associated with pCR in ER+/HER2+ Tumors

Total tumor-infiltrating lymphocytes (tTIL) have been proposed as a predictor of pCR in triple negative breast cancer (Andre et al., *Clinical Cancer Research* 19:28-33, 2013). However, the association between tTILs and pCR in ER2+/HER2+ tumors remains uncertain. Higher levels of tTILs identified ER+/HER2+ tumors with pCR in the 50 cases used for ColXα1 IHC (Table 2).

The abundance of tumor-associated stroma and tTILs were evaluated in the 74 ER2+/HER2+ tumor cohort. The associations with pCR were observed for both stroma and TIL (Tables 2 and 4). Age, high grade, stage, and lymph node status were not significant predictive factors. The combination of stromal score and tTIL is a good predictor in ER2+/HER2+ tumors.

TABLE 4

Univariate and multivariate Logistic Regression for prediction of pCR in ER+/HER2+. N = 74.

|  |  | HR (95% CI) | P value |
|---|---|---|---|
| Age |  | 1.04 (1.003-1.08) | 0.04 |
| tTIL |  | 0.93 (0.9-0.96) | <1 × 10⁻³ |
| Stroma |  | 9.3 (3.0-28.7) | <1 × 10⁻³ |
| Multivariate |  |  |  |
| Age + stroma | Age | 1.03 (0.99-1.07) | 0.14 |
|  | stroma | 8.5 (2.7-26.3) | <1 × 10⁻³ |
| Age + tTIL | Age | 1.02 (0.97-1.07) | 0.44 |
|  | tTIL | 0.93 (0.91-0.96) | <1 × 10⁻³ |
| tTIL + Stroma | tTIL | 0.93 (0.9-0.97) | <1 × 10⁻³ |
|  | stroma | 9.8 (2.1-44.3) | 0.003 |

Combination of ColXα1 and tTIL Predicts Neoadjuvant Chemotherapy Response

In the 50 patients tested with ColXα1 IHC scoring, the combination of tTIL and ColXα1 score was a good predictor in a multivariate logistic regression model. The amount of tumor-associated stroma was modestly associated with pCR (Table 2) and univariate analysis showed association with pCR (Table 3). But multivariate analysis suggested that stroma contributed to pCR predictions when combined with nodal status or lymphocytes, but not with ColXα1 signal (Table 3). This may be consistent with ColXα1 staining representing a specific fraction of stroma. Together, these observations suggest that ColXα1 identifies a subset of stroma, particularly important for chemotherapy sensitivity. This suggests that the combination of tTIL and ColXα1 may be a good biomarker to predict pCR.

In subjects with stage II-III breast cancer, achievement of a pathologic complete response to NAC correlates with improved long-term outcomes, but the predictive value of the standard clinical biomarkers such ER, HER2, and PR is limited. The HER2 group of subjects generally show a significantly higher pCR rate in response to NAC+H therapy. However, within the HER2+ population, pCR was more common for ER-tumors than for ER+ tumors, suggesting a possibility that for a subset of HER2+ tumors, response is driven at least partially by ER, and ER+/HER2+ tumors are biologically different than ER-/HER2+ tumors (Cortazar et al., *The Lancet* 384:164-172, 2014; Nahta, *Breast Cancer Research And Treatment* 135:39-48, 2012). Genome-wide expression analysis ER+/HER2+ tumors correlated with post-treatment pathologic response. Microenvironment factors such as collagens and immune cells were found to predict response. Specifically, aberrant expression of the Col10A1 gene was associated with poor pathologic response.

In the past, most analyses of factors influencing pCR rates have focused on the cancer cells; only recently has the potential significance of tumor microenvironment and tumor-stromal interactions become appreciated. The tumor microenvironment is complex, consisting mainly of tumor epithelial cells and cancer-associated fibroblasts (Rozenchan et al., *International Journal of Cancer* 125:2767-2777, 2009). Collagen is a major component of the ECM (Luparello, *Journal of Carcinogenesis & Mutagenesis* S13, 2013). ColXα1 expression levels in ER+/HER2+ tumors have a bimodal distribution, an important characteristic for a biomarker. Many ER+/HER2+ tumors do not express ColXα1 as detected by IHC. While other collagens may be expressed in these tumors thus compensating for the absence of ColXα1, stroma expressing ColXα1 is strongly associated with drug resistance.

Col10A1 expression is up-regulated in a variety of human malignancies, including breast cancer (Chapman et al., *Future Oncology* 8:1031-1040, 2012). Col10A1 has been found in a number of stroma gene expression signatures. It is up-regulated in cancer-associated fibroblasts compared to normal fibroblasts (Bauer et al., *Oncogene* 29:1732-1740, 2010; Planche et al., *PloS ONE* 6:e18640, 2011). Col10A1 is part of breast cancer signatures, including a CD10+ signature to discriminate in situ from invasive breast cancer (Desmedt et al., *Clinical Cancer Research* 18:1004-1014, 2012), and a stroma expression signature to predict resistance to NAC in breast cancer (Farmer et al., *Nature Medicine* 15:68-74, 2009). As described herein, the present disclosure connects ColXα1 protein levels to chemotherapy outcomes. Collagen was highly expressed in breast tumors contributing to its dense structure (Luparello, *Journal of Carcinogenesis & Mutagenesis* S13, 2013). The relationship between collagen and chemotherapy response has not been defined in breast tumors. Collagen is one of the most abundant proteins. Increased protein translation in combination with the very stable triple helix structure suggests that the dynamic range of protein measurements is larger than that observed in mRNA (Shoulders et al., *Annual Review of Biochemistry* 2009; 78:929-958. doi: 10.1146/annurev.biochem.77.032207.120833; and Stefanovic, *Wiley Interdiscip Rev RNA*. 2013; 4(5):535-545. doi: 10.1002/wrna. 1177. PubMed PMID: 23907854; PubMed Central PMCID: PMC3748166). Furthermore, examination of collagen distribution by IHC can provide spatial insights not as readily obtainable by mRNA analysis. Similar results are possible with IHC targeting Col14A1 and Col3A1, or a combination of collagen antibodies may provide improved specificity and sensitivity to predict pCR. In a separate set of 32 triple negative breast cancer cases treated with NAC, however, Col10A1 mRNA and ColXα1 protein expression was not associated with pCR. This suggests that ColXα1 rich stroma interacts with hormone and/or growth factor signaling to mediate chemotherapy response.

Many studies have found that higher tTILs were associated with better clinical outcome in triple negative breast cancer (Denkert et al., *Journal of Clinical Oncology* 28:105-113, 2010; West et al., *Breast Cancer Research* 13:R126, 2011; Ono et al., *Breast Cancer Research and Treatment* 132:793-805, 2012; Yamaguchi et al., *Human 5 Pathology* 43:1688-1694, 2012; Lee et al., *Journal of Breast Cancer* 16:32-39, 2013; Seo et al., *British Journal of Cancer* 109: 2705-2713, 2013; Adams et al., *Journal of Clinical Oncology*, 2014, doi: 10.1200/JCO.2013.55.0491. PubMed PMID: 25071121; Dieci et al., *Annals of Oncology* 25:611-618, 2014). As described herein, higher levels of TILs correlated with pCR in ER+/HER2+ breast cancers. Thus, measurement of tTILs combined with ColXα1 expression will help identify subjects most likely to respond to NAC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject diagnosed as having estrogen receptor positive and human epidermal growth factor receptor 2 positive breast cancer, the method comprising:
   detecting in a sample comprising cancerous breast tissue from the subject an expression level of collagen type 10 alpha 1 that is the same or lower than a collagen type 10alpha 1 reference level, wherein the reference level is the average expression level of collagen type 10 alpha 1 obtained from a population of ER+/HER2+ breast tumors; and
   administering a neoadjuvant or adjuvant chemotherapy to the subject.

2. The method of claim 1, further comprising detecting in the sample an expression level of collagen type 3 alpha 1.

3. The method of claim 1, further comprising detecting in the sample an expression level of collagen type 14 alpha 1.

4. The method of claim 1, further comprising detecting in the sample a total level of tumor infiltrating T lymphocytes (tTILs).

5. The method of claim 1, further comprising detecting in the sample a level of tumor-associated stroma.

6. The method of claim 1, wherein the expression level of collagen type 10 alpha 1 is detected by Northern blot or qPCR analysis of mRNA.

7. The method of claim 1, wherein the expression level of collagen type 10 alpha 1 is detected by immunohistochemistry.

8. The method of claim 2, wherein the expression level of collagen type 3 alpha 1 is detected by Northern blot or qPCR analysis of mRNA.

9. The method of claim 2, wherein the expression level of collagen type 3 alpha 1 is detected by immunohistochemistry.

10. The method of claim 3, wherein the expression level of collagen type 14 alpha 1 is detected by Northern blot or qPCR analysis of mRNA.

11. The method of claim 3, wherein the expression level of collagen type 14 alpha 1 is detected by immunohistochemistry.

12. The method of claim 1, wherein the neoadjuvant chemotherapy comprises administering docetaxel, carboplatin, doxorubicin, cyclophosphamide, paclitaxel, or a combination thereof.

13. The method of claim 1, wherein the adjuvant chemotherapy comprises administering docetaxel, carboplatin, doxorubicin, cyclophosphamide, paclitaxel, or a combination thereof.

14. The method of claim 1, wherein the administering further comprises administering a HER2-targeted therapy.

15. The method of claim 14, wherein the HER2-targeted therapy comprises administering trastuzumab, pertuzumab, lapatinib, or a combination thereof.

16. The method of claim 1, wherein the subject is human.

* * * * *

UNITED STATES PATENT AND TRADEMARK OFFICE
CERTIFICATE OF CORRECTION

PATENT NO. : 9,784,743 B2
APPLICATION NO. : 15/187279
DATED : October 10, 2017
INVENTOR(S) : Alexander S. Brodsky, Yihong Wang and Murray Resnick It is certified that error appears in the above-identified patent and that said Letters Patent is hereby corrected as shown below:

In the Claims

In Column 20, Line 13 (Approx.), Claim 1, delete "10alpha" and insert -- 10 alpha --

Signed and Sealed this
First Day of May, 2018

Andrei Iancu
*Director of the United States Patent and Trademark Office*